(12) United States Patent
Camargo et al.

(10) Patent No.: US 11,709,130 B2
(45) Date of Patent: Jul. 25, 2023

(54) SIGNAL OUTPUT APPARATUS AND CONCENTRATION MEASUREMENT SYSTEM

(71) Applicant: ASAHI KASEI MICRODEVICES CORPORATION, Tokyo (JP)

(72) Inventors: Edson Gomes Camargo, Tokyo (JP); Hiroyuki Kato, Tokyo (JP)

(73) Assignee: Asahi Kasel Microdevices Corporation, Tokyo (JP)

( * ) Notice: Subject to any disclaimer, the term of this patent is extended or adjusted under 35 U.S.C. 154(b) by 80 days.

(21) Appl. No.: 17/494,924

(22) Filed: Oct. 6, 2021

(65) Prior Publication Data

US 2022/0113248 A1    Apr. 14, 2022

(30) Foreign Application Priority Data

Oct. 9, 2020 (JP) ................................. 2020-171373
Aug. 26, 2021 (JP) ................................. 2021-137674

(51) Int. Cl.
*G01N 21/3504* (2014.01)
*G01N 33/00* (2006.01)
*G01K 13/00* (2021.01)

(52) U.S. Cl.
CPC ......... *G01N 21/3504* (2013.01); *G01K 13/00* (2013.01); *G01N 33/0027* (2013.01); *G01N 2201/12753* (2013.01)

(58) Field of Classification Search
CPC ........... G01N 21/3504; G01N 33/0027; G01N 2201/12753; G01K 13/00
See application file for complete search history.

(56) References Cited

U.S. PATENT DOCUMENTS

2004/0267151 A1* 12/2004 Eckerbom ............ G01N 33/497
600/532
2014/0008526 A1    1/2014 Zeng et al.
(Continued)

FOREIGN PATENT DOCUMENTS

JP    2001-153723 A    6/2001
JP    2011-095143 A    5/2011
(Continued)

*Primary Examiner* — Kiho Kim
(74) *Attorney, Agent, or Firm* — Morgan, Lewis & Bockius LLP

(57) ABSTRACT

Signal output apparatus and concentration measurement system has a light receiving unit and an interface unit provided at a support unit. Light receiving unit receives infrared rays emitted to a measurement target substance, and outputs a detection signal according to received infrared rays. Storage unit stores a parameter according to a characteristic of at least one of a plurality of components including the light receiving unit, the parameter being used for concentration computation of the measurement target substance, as a calibration parameter. Interface unit outputs an output signal including a calibration parameter signal according to the calibration parameter input from the storage unit and a signal based on the detection signal input from the light receiving unit to a signal computation processing unit, without executing the concentration computation. The signal output apparatus corrects a deviation caused by a characteristic variation of each apparatus to realize concentration measurement with high accuracy.

20 Claims, 5 Drawing Sheets

(56) References Cited

U.S. PATENT DOCUMENTS

| | | |
|---|---|---|
| 2017/0163919 A1 | 6/2017 | Kawai |
| 2018/0184497 A1 | 6/2018 | Fujita et al. |
| 2020/0145011 A1 | 5/2020 | Sato et al. |

FOREIGN PATENT DOCUMENTS

| | | |
|---|---|---|
| JP | 2011-119398 A | 6/2011 |
| JP | 2011-203004 A | 10/2011 |
| JP | 2012-230077 A | 11/2012 |
| JP | 2017-044577 A | 3/2017 |
| JP | 2019-028037 A | 2/2019 |
| JP | 2020-077916 A | 5/2020 |
| WO | 2016/051847 A1 | 4/2016 |

\* cited by examiner

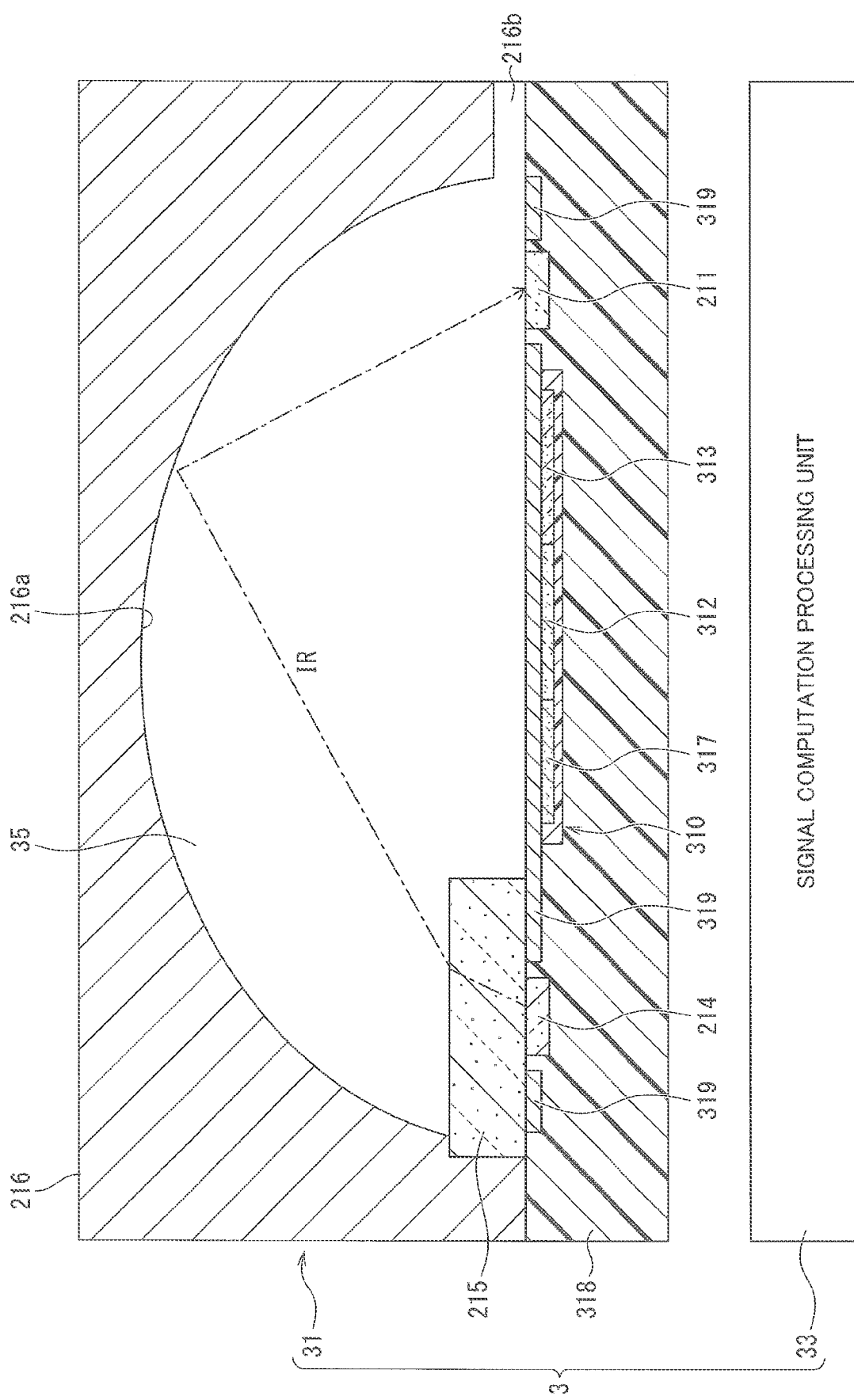

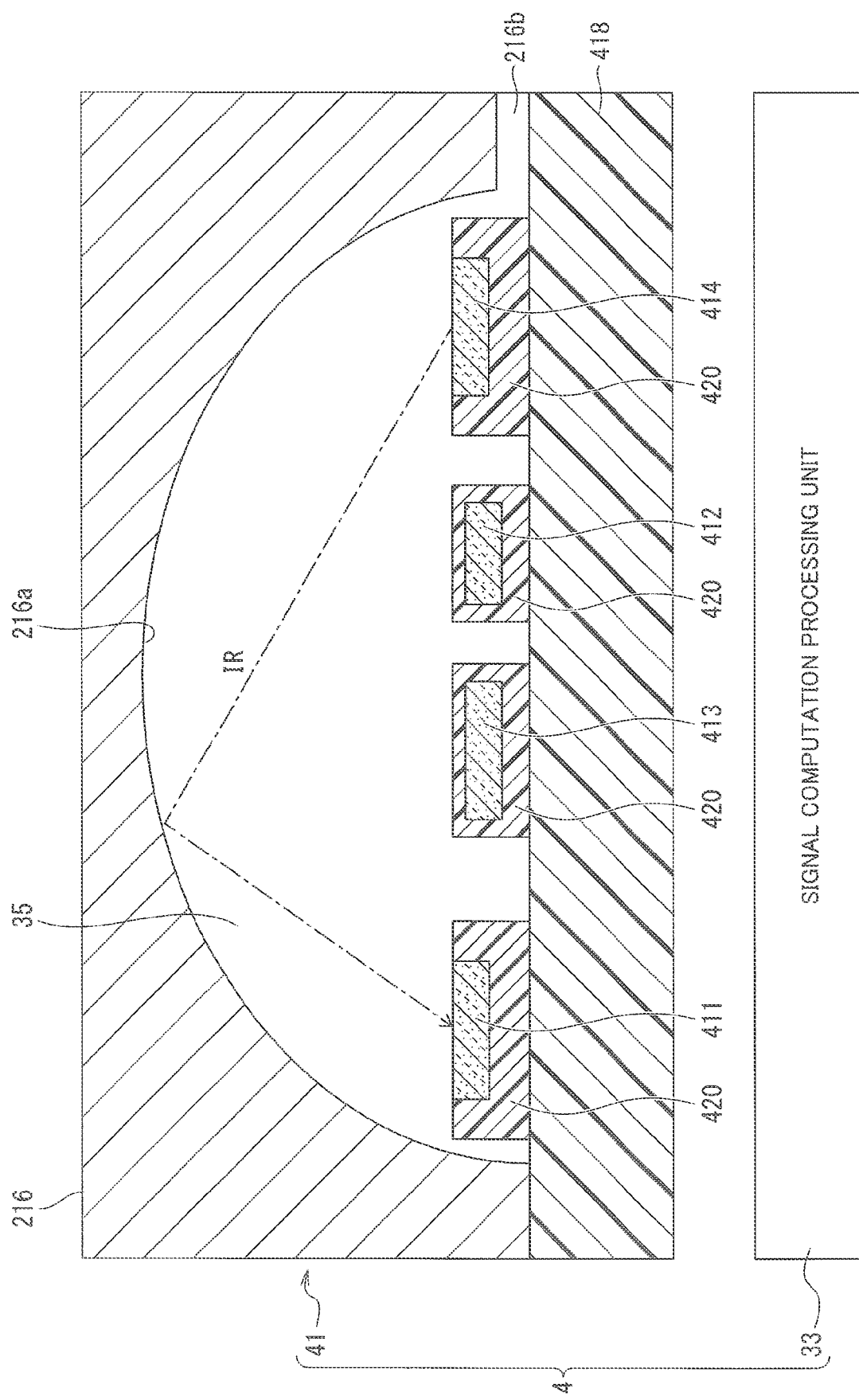

SIGNAL OUTPUT APPARATUS AND CONCENTRATION MEASUREMENT SYSTEM

BACKGROUND OF THE INVENTION

Field of the Invention

The present invention relates to a signal output apparatus for a concentration measurement system, and the concentration measurement system.

Description of the Related Art

For example, PTL 1 discloses a quantum type infrared gas concentration meter that computes a concentration of a measurement target substance based on a detection signal according to received infrared rays.

CITATION LIST

Patent Literature

PTL 1: JP 2011-203004 A

SUMMARY OF THE INVENTION

In conventional infrared gas density meters, it is possible to compute the concentration of the measurement target substance by a predetermined computation process. Meanwhile, there is a problem that it is difficult to correct a deviation caused by a characteristic variation of each element constituting the quantum type infrared gas concentration meter.

The quantum type infrared gas concentration meter described in PTL 1 in the related art has computation means, and by using a desired calibration parameter with this computation means, it is possible to accurately compute the concentration of the measurement target substance. Meanwhile, the computing means has a larger size in the entire quantum type infrared gas concentration meter, which hinders miniaturization of the entire apparatus.

On the other hand, in a case where the computation means is performed by an external apparatus, it is not easy for the computation means to correct the deviation caused by a characteristic variation of each quantum type infrared gas concentration meter. That is, it is necessary to connect the external apparatus having the computation means and the quantum type infrared gas concentration meter, to perform calibration in a desired environment, and to store the calibration parameters obtained by the calibration in the computation means, so it is not possible to easily realize gas concentration measurement with high accuracy.

That is, an object of the present invention is to provide a miniaturized signal output apparatus and concentration measurement system capable of easily correcting a deviation caused by a characteristic variation of each element and realizing concentration measurement with high accuracy.

According to an aspect of the present invention, there is provided a signal output apparatus including: a support unit; a light receiving unit provided at the support unit, and configured to receive infrared rays emitted to a measurement target substance, and output a detection signal according to the received infrared rays; a storage unit provided at the support unit, and configured to store a parameter according to a characteristic of at least one of a plurality of components including the light receiving unit, the parameter being used for concentration computation of the measurement target substance, as a calibration parameter; and an interface unit provided at the support unit, and configured to output an output signal including a calibration parameter signal according to the calibration parameter input from the storage unit and a signal based on the detection signal input from the light receiving unit to a signal computation processing unit externally provided, without executing the concentration computation.

Further, according to another aspect of the present invention, there is provided a concentration measurement system including: the signal output apparatus according to the aspect of the present invention; and the signal computation processing unit provided outside the signal output apparatus and configured to compute a concentration of the measurement target substance on the basis of the signal based on the detection signal and the calibration parameter signal included in the output signal input from the interface unit.

Further, according to still another aspect of the present invention, there is provided a concentration measurement system including: the signal output apparatus according to the aspect of the present invention; and the signal computation processing unit provided outside the signal output apparatus and configured to compute a concentration of the measurement target substance on the basis of the signal based on the detection signal and the calibration parameter signal included in the output signal input from the interface unit, and a drive signal for driving the light emitting unit.

With the signal output apparatus according to one aspect of the present invention and the concentration measurement system according to each aspect of the present invention, it is possible to easily correct a deviation caused by a characteristic variation of each element and realize concentration measurement with high accuracy, and it is possible to reduce a size.

BRIEF DESCRIPTION OF THE DRAWINGS

FIG. 4 is a schematic cross-sectional view illustrating an example of a schematic configuration of the signal output apparatus and the concentration measurement system according to the third embodiment of the present invention.

FIG. 5 is a schematic cross-sectional view illustrating an example of a schematic configuration of a signal output apparatus and a concentration measurement system according to a modification example of the third embodiment of the present invention.

DESCRIPTION OF THE PREFERRED EMBODIMENTS

Hereinafter, the present invention will be described through embodiments of the invention, but the following embodiments do not limit the invention according to the claims. Further, not all combinations of features described in the embodiments are fundamental to solving means of the invention.

First Embodiment

Figure 1:
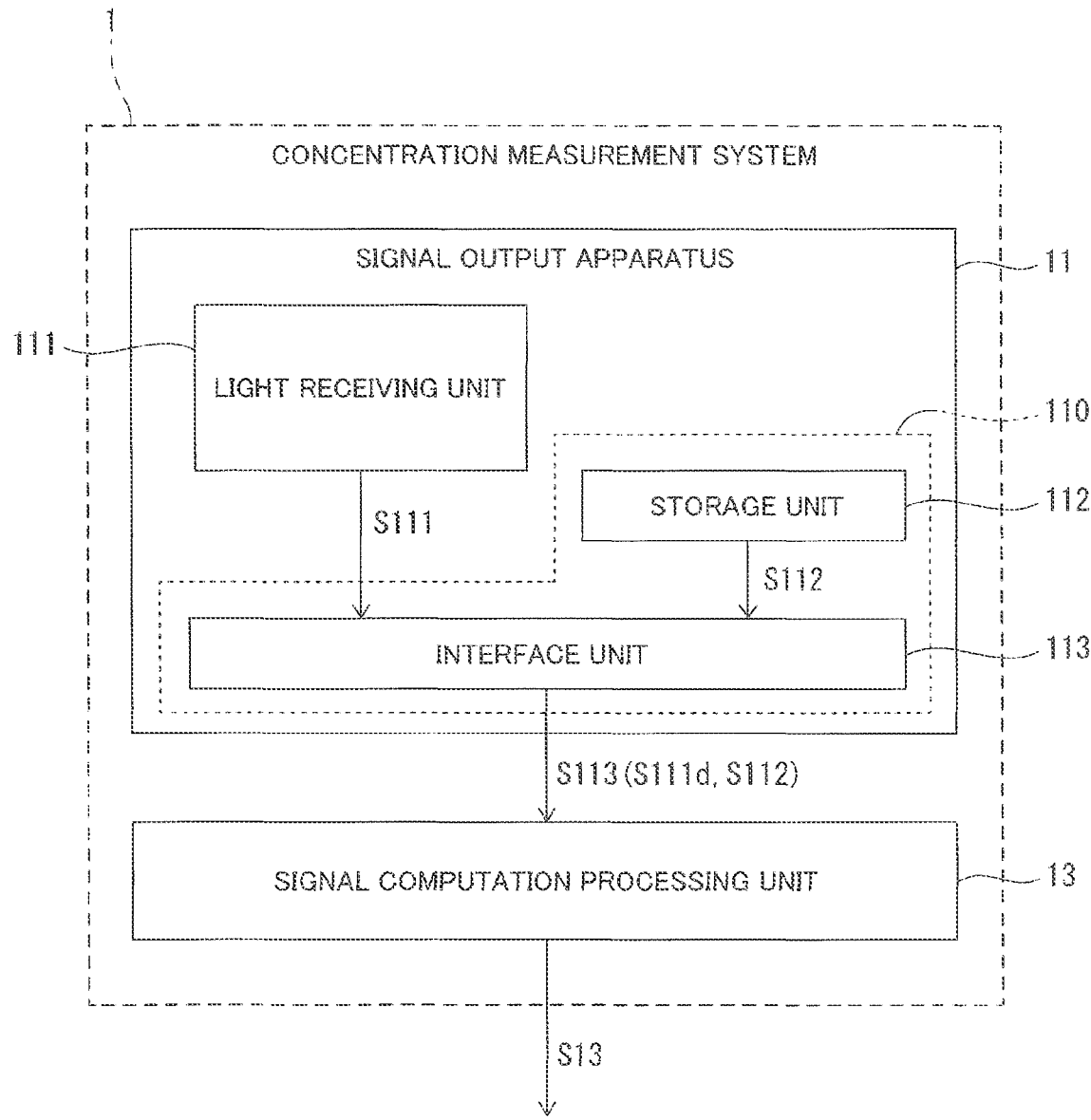
FIG. 1 is a block diagram illustrating an example of a schematic configuration of a signal output apparatus and a concentration measurement system according to a first embodiment of the present invention.

A signal output apparatus and a concentration measurement system according to a first embodiment of the present invention will be described with reference to FIG. 1. FIG. 1 is a block diagram illustrating an example of a schematic configuration of a signal output apparatus 11 and a concentration measurement system 1 according to the present embodiment. Hereinafter, as the signal output apparatus according to the present embodiment, the signal output apparatus 11 for the concentration measurement system will be described as an example.

As illustrated in FIG. 1, the signal output apparatus 11 according to the present embodiment includes a light receiving unit 111 that receives infrared rays (IRs) emitted to a measurement target substance, and outputs a detection signal S111 according to the received infrared rays. In addition, the signal output apparatus 11 includes a storage unit 112 that stores a parameter according to a characteristic of at least one of a plurality of components including the light receiving unit 111, the parameter being used for computing a concentration of the measurement target substance, as a calibration parameter. That is, the storage unit 112 stores a parameter according to a characteristic of the signal output apparatus 11 (that is, the characteristic of the component of the signal output apparatus 11) as the calibration parameter. Further, the signal output apparatus 11 includes an interface unit 113 that outputs an output signal S113 including a calibration parameter signal S112 according to the calibration parameter input from the storage unit 112 and a signal based on the detection signal S111 input from the light receiving unit 111 to a signal computation processing unit 13 externally provided, without executing concentration computation. The interface unit 113 is electrically connected to the light receiving unit 111 and the storage unit 112. The light receiving unit 111 is configured with, for example, a photodetector. The signal output apparatus 11 includes a support unit that supports the light receiving unit 111, the storage unit 112, and the interface unit 113 (see FIG. 4). The light receiving unit 111, the storage unit 112, and the interface unit 113 are provided on the support unit.

The "calibration parameter signal according to calibration parameter" is a signal configured to extract the calibration parameter. Further, a "calibration parameter signal according to parameter", which will be described below is a signal configured to extract the parameter. The concepts of "calibration parameter signal according to calibration parameter" and "calibration parameter signal according to parameter" are the same in a second embodiment and a third embodiment, which will be described below.

The concept of "output signal S113 includes calibration parameter signal S112 and signal based on detection signal S111" includes the concept that the calibration parameter signal S112 and the signal based on the detection signal S111 individually output from the signal output apparatus 11 to the signal computation processing unit 13 are collectively referred to as the output signal S113. Further, the concept of "output signal S113 includes calibration parameter signal S112 and signal based on detection signal S111" includes the concept that the calibration parameter signal S112 and the signal based on the detection signal Sill converted into a format compliant with a signal standard for transmitting and receiving signals between predetermined components are embedded in the output signal S113.

Further, the output signal S113 includes a digital detection signal S111$d$. The analog detection signal S111 output from the light receiving unit 111 and the digital detection signal S111$d$ are signals having identical information except for signal formats. Therefore, in the present embodiment, the signal based on the detection signal Sill means a signal actually included, between the analog detection signal S111 and the digital detection signal S111$d$. That is, in a case where the output signal S113 includes the digital detection signal S111$d$ as in the present embodiment, the signal based on the detection signal S111 becomes the detection signal S111$d$. On the other hand, in a case where the output signal S113 includes the analog detection signal S111, the signal based on the detection signal S111 becomes the detection signal S111.

The detection signal S111 output by the light receiving unit 111 or the calibration parameter signal S112 output by the storage unit 112 is input to the interface unit 113. The interface unit 113 may be configured to have a function of amplifying the input detection signal S111 and analog-to-digital converting the amplified detection signal S111 to generate the digital detection signal S111$d$. As described above, the interface unit 113 may be configured to amplify the detection signal S111 or perform analog-to-digital conversion, and is configured not to execute the computation process of the detection signal S111.

The signal output apparatus 11 may include an amplification unit that amplifies the detection signal S111 output by the light receiving unit 111, and an analog-to-digital conversion unit that analog-to-digital converts the detection signal S111 amplified by the amplification unit and outputs the digital detection signal S111$d$ to the interface unit 113.

Further, the signal output apparatus 11 includes an integrated circuit 110 in which the storage unit 112 and the interface unit 113 are integrated, from the viewpoint of miniaturization. Meanwhile, the signal output apparatus 11 also may have a configuration in which the storage unit 112 and the interface unit 113 are not integrated.

As illustrated in FIG. 1, the concentration measurement system 1 according to the present embodiment includes the signal output apparatus 11 having the above configuration, and the signal computation processing unit 13 that is provided outside the signal output apparatus 11 and configured to compute a concentration of the measurement target substance (not illustrated) on the basis of the signal based on the detection signal S111 and the calibration parameter signal S112 included in the output signal S113 input from the interface unit 113. The signal computation processing unit 13 is configured to output a computation result as a concentration signal S13 from the concentration measurement system 1. Here, the "external" means a portion outside the signal output apparatus 11, specifically, a portion not included in the signal output apparatus 11 supported by the support unit, and the "externally provided" means being not provided in the support unit and being not integrated with the signal output apparatus 11.

The storage unit 112 stores a parameter according to a characteristic of the light receiving unit 111 among the plurality of components included in the signal output apparatus 11, as a calibration parameter, and outputs the calibration parameter signal S112 according to the calibration parameter to the interface unit 113. The interface unit 113 outputs the output signal S113 including the detection signal S111 input from the light receiving unit 111 and the calibration parameter signal S112 input from the storage unit 112 to the signal computation processing unit 13 externally provided.

The concentration measurement system 1 outputs the calibration parameter signal S112 stored in advance in the storage unit 112 from the signal output apparatus 11 to the signal computation processing unit 13, and causes the signal computation processing unit 13 corresponding to an external unit when viewed from the signal output apparatus 11 to correct the concentration computation of the measurement target substance by using the calibration parameter signal S112. The storage unit 112 stores the parameter according to the characteristic of the light receiving unit 111 (for example, at least one of optical characteristics and electrical characteristics) as the parameter according to the characteristic of at least one of the plurality of components included in the signal output apparatus 11. The interface unit 113 is able to include the calibration parameter signal S112 according to the parameter of the characteristic of the light receiving unit 111 (that is, the parameter according to the characteristic of the light receiving unit 111) in the output signal S113, and output the output signal S113 to the signal computation processing unit 13. Therefore, the concentration measurement system 1 is able to output the concentration signal S13 corrected according to the characteristic peculiar to each component (the light receiving unit 111 in the present embodiment) provided in the signal output apparatus 11. In a case where the parameter according to the characteristic of the light receiving unit 111 stored in the storage unit 112 is a parameter for correcting a characteristic variation of the light receiving unit 111, the signal computation processing unit 13 is able to generate and output the concentration signal S13 corrected for the characteristic variation of the light receiving unit 111. Here, the characteristic variation of the light receiving unit 111 is, for example, a variation in a photoelectric conversion characteristic due to a variation in electrical characteristics of a photodetector constituting a photoelectric conversion unit of the light receiving unit 111, a variation in a voltage or a current of the output signal due to a variation in electrical characteristics of a photodetector constituting an output unit of the light receiving unit 111, or the like.

The calibration parameter signal S112 is not particularly limited as long as the concentration computation of the measurement target substance is able to be corrected as a result, for example, according to the characteristic of the light receiving unit 111. That is, the calibration parameter signal S112 is not particularly limited as long as the concentration computation of the measurement target substance is able to be corrected as a result, for example, according to the characteristic variation of the light receiving unit 111. In a case where the signal computation processing unit 13 applies the input detection signal S111 to, for example, a predetermined equation to compute the concentration, the parameter that the calibration parameter signal S112 has may be used as a coefficient of the predetermined equation. In a case where the predetermined equation is able to be expressed by the cubic function of "$y = a \times x^3 + b \times x^2 + c \times x + d$", the coefficients a, b, c, and d may be parameters that the calibration parameter signal has (that is, the calibration parameters stored in the storage unit 112). In the cubic function, y may be a concentration result of the measurement target substance, and x may be a signal according to the detection signal S111 output from the light receiving unit 111.

Further, in the signal output apparatus 11 according to the present embodiment, the interface unit 113 includes the calibration parameter signal S112 in the output signal S113, and outputs the output signal S113 to the signal computation processing unit 13, without executing the concentration computation. The interface unit 113 does not execute not only the concentration computation using the calibration parameter included in the calibration parameter signal S112 but also the concentration computation not using the calibration parameter. Here, the concentration computation includes correction of the output signal according to the concentration, in addition to the actual concentration computation. That is, the signal output apparatus 11 does not include a computation unit that computes based on the input signal. Therefore, the signal output apparatus 11 and the concentration measurement system 1 are able to reduce a thermal influence or an electromagnetic influence exerted on the light receiving unit 111 by heat and electromagnetic waves generated by the computation operation of the computation unit. As a result, the concentration measurement system 1 is able to measure the concentration of the measurement target substance with high accuracy.

For example, the storage unit 112 stores a plurality of parameters according to the characteristics of the light receiving unit 111 as the parameters according to the characteristics of at least one of the plurality of components included in the signal output apparatus 11, as calibration parameters. The storage unit 112 stores, for example, parameters associated with a magnitude of the characteristic variation of the light receiving unit 111 as the calibration parameters. In a shipping inspection of the concentration measurement system 1, concentration measurement of a standard measurement target substance having a known concentration is repeatedly executed while changing the parameters. The concentration measurement system 1 sets a parameter at which a concentration closest to the known concentration is obtained, as a calibration parameter used in actual operation. As a result, the concentration measurement system 1 is able to measure the concentration of the measurement target substance according to the characteristic of the light receiving unit 111 (for example, the characteristic variation of the light receiving unit). Such a setting of the calibration parameter according to the characteristic of the light receiving unit 111 is not limited to the shipping inspection of the concentration measurement system 1, and may be executed before the operation of the concentration measurement system 1.

The calibration parameter according to the characteristic of the light receiving unit 111 may be set by, for example, a control unit (not illustrated) which is provided in the signal output apparatus 11 and collectively controls the signal output apparatus 11 and a control unit which is provided in the signal computation processing unit 13 and collectively controls the signal computation processing unit 13. Further, the calibration parameter according to the characteristic of the light receiving unit 111 may be set by, for example, a control unit (not illustrated) which is provided in the concentration measurement system 1 and collectively controls both the signal output apparatus 11 and the signal computation processing unit 13.

As described above, the signal output apparatus 11 according to the present embodiment includes the support unit, the light receiving unit 111 that is provided at the support unit and receives infrared rays emitted to the measurement target substance and outputs the detection signal S111 according to the received infrared rays, the storage unit 112 that is provided at the support unit and stores the parameters according to the characteristics of at least one of the plurality of components including the light receiving unit ill, the parameter being used for computing the concentration of the measurement target substance, as calibration parameters, and the interface unit 113 that is provided in the support unit, and is able to output the output signal S113 including the calibration parameter signal S112 according to the calibration parameter input from the storage unit 112 and the signal based on the detection signal S111 input from the light receiving unit 111 to the signal computation processing unit 13 externally provided, without executing the concentration computation.

In addition, the concentration measurement system 1 according to the present embodiment includes the signal output apparatus 11 according to the present embodiment, and the signal computation processing unit 13 that is provided outside the signal output apparatus 11 and configured to compute a concentration of the measurement target substance on the basis of the signal based on the detection signal S111 and the calibration parameter signal S112 included in the output signal S113 input from the interface unit 113.

As a result, the signal output apparatus 11 and the concentration measurement system 1 are able to easily correct a deviation caused by a characteristic variation of each apparatus (the light receiving unit 111 in the present embodiment), and realize concentration measurement with high accuracy, and it is possible to reduce a size.

Second Embodiment

Figure 2:
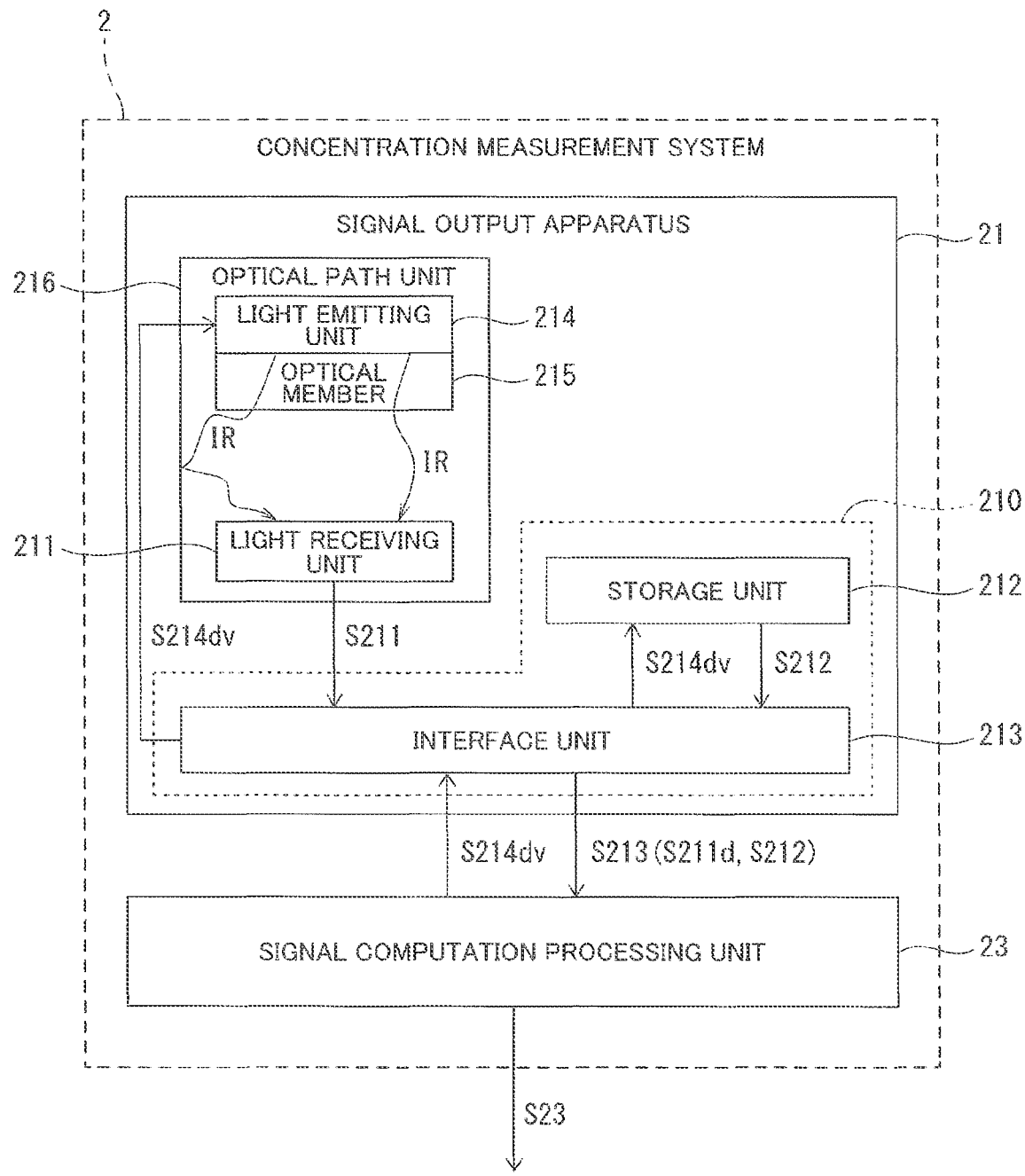
FIG. 2 is a block diagram illustrating an example of a schematic configuration of a signal output apparatus and a concentration measurement system according to a second embodiment of the present invention.

A signal output apparatus and a concentration measurement system according to the second embodiment of the present invention will be described with reference to FIG. 2. FIG. 2 is a block diagram illustrating an example of a schematic configuration of a signal output apparatus 21 and a concentration measurement system 2 according to the present embodiment. Hereinafter, as the signal output apparatus according to the present embodiment, the signal output apparatus 21 for the concentration measurement system will be described as an example.

As illustrated in FIG. 2, the signal output apparatus 21 according to the present embodiment includes a light receiving unit 211 that receives infrared rays emitted to a measurement target substance, and outputs a detection signal S211 according to the received infrared rays. In addition, the signal output apparatus 21 includes a storage unit 212 that stores parameters according to characteristics of at least one of a plurality of components including the light receiving unit 211, the parameter being used for computing a concentration of the measurement target substance, as calibration parameters. Further, the signal output apparatus 21 includes an interface unit 213 capable of outputting an output signal S213 including a calibration parameter signal S212 according to the calibration parameter input from the storage unit 212 and a signal based on the detection signal S211 input from the light receiving unit 211 to a signal computation processing unit 23 externally provided, without executing concentration computation. The interface unit 213 is electrically connected to the light receiving unit 211 and the storage unit 212. The light receiving unit 211 is configured with, for example, a photodetector. The signal output apparatus 21 includes a support unit that supports the light receiving unit 211, the storage unit 212, and the interface unit 213 (see FIG. 4). The light receiving unit 111, the storage unit 112, and the interface unit 113 are provided on the support unit.

The concept of "output signal S213 includes calibration parameter signal S212 and signal based on detection signal S211" has the same concept of "output signal S113 includes calibration parameter signal S112 and signal based on detection signal S111" in the first embodiment. Further, in the same manner as the interface unit 113 in the first embodiment, the interface unit 213 may be configured to have a function of amplifying the input detection signal S211 and analog-to-digital converting the amplified detection signal S211 to generate a digital detection signal S211$d$. In this case, the output signal S213 includes the digital detection signal S211$d$. The interface unit 213 may be configured to amplify the detection signal S211 or perform analog-to-digital conversion, and is configured not to execute a concentration computation process of the detection signal S211.

Here, the output signal S213 includes the digital detection signal S211$d$. The analog detection signal S211 output from the light receiving unit 211 and the digital detection signal S211$d$ are signals having identical information except for signal formats. Therefore, in the present embodiment, the signal based on the detection signal S211 means a signal actually included, between the analog detection signal S211 and the digital detection signal S211$d$. That is, in a case where the output signal S213 includes the digital detection signal S211$d$ as in the present embodiment, the signal based on the detection signal S211 becomes the detection signal S211$d$. On the other hand, in a case where the output signal S213 includes the analog detection signal S211, the signal based on the detection signal S211 becomes the detection signal S211.

As illustrated in FIG. 2, as compared with the signal output apparatus 11 according to the first embodiment, the signal output apparatus 21 includes a light emitting unit 214 that emits infrared rays, and at least one of an optical member 215 disposed in an optical path through which the infrared rays emitted by the light emitting unit 214 reach the light receiving unit 211 or an optical path unit 216 that guides the infrared rays emitted by the light emitting unit 214 to the light receiving unit 211, as the plurality of components. That is, in the present embodiment, in addition to the light receiving unit 211, the plurality of components include at least one of the light emitting unit 214 that is provided at the support unit (not illustrated) and emits infrared rays, the optical member 215 provided at the support unit and disposed in an optical path through which the infrared rays emitted by the light emitting unit 214 reach the light receiving unit 211 or the optical path unit 216 that is provided at the support unit and guides the infrared rays emitted by the light emitting unit 214 to the light receiving unit 211. As described above, the signal output apparatus 21 according to the present embodiment includes the light emitting unit 214, the optical member 215, and the optical path unit 216, as the plurality of components. Here, the light emitting unit 214, the optical member 215, and the optical path unit 216 are also supported by the support unit (see FIG. 4). The light emitting unit 214 is configured with, for example, a light emitting diode. The optical member 215 is made of a material (for example, silicon) capable of transmitting infrared rays. The optical member 215 may be a so-called optical filter or the like having a function of selectively transmitting infrared rays incident from the light emitting unit 214 in a predetermined wavelength bandwidth. As a result, for the infrared rays emitted by the light emitting unit 214, only a wavelength bandwidth absorbed by the measurement target substance is able to be selected, and measurement with high sensitivity and high accuracy becomes possible. The optical member 215 may be provided in the vicinity of the light emitting unit 214, in the vicinity of the light receiving unit 211, or in the middle (optical path) until the light output from the light emitting unit 214 is incident on the light receiving unit 211. The optical path unit 216 is made of a material capable of reflecting infrared rays (for example, aluminum). Further, the optical path unit 216 may have a reflective film made of a material capable of reflecting infrared rays on a surface on which the infrared rays are incident. The optical path unit 216 reflects infrared rays passing through the measurement target substance once or a plurality of times, and guides the infrared rays to the light receiving unit 211. As a result, the signal output apparatus 21 is able to improve light reception efficiency of the light receiving unit 211 of the infrared rays passing through the measurement target substance. As a result, the concentration measurement system 2 according to the present embodiment is able to improve detection accuracy of the concentration of the measurement target substance.

The storage unit 212 stores the parameter according to the characteristic of the light receiving unit 211 as a parameter according to a characteristic of at least one of the plurality of components included in the signal output apparatus 21, as calibration parameters. Further, the storage unit 212 stores at least one of parameters according to characteristics of components other than the light receiving unit 211 among the plurality of provided components, as the parameters according to the characteristics of at least one of the plurality of components included in the signal output apparatus 21, as the calibration parameters. In the present embodiment, the light emitting unit 214, the optical member 215, and the optical path unit 216 correspond to the components other than the light receiving unit 211 among the plurality of components. Here, each characteristic of the light receiving unit 211 and the light emitting unit 214 is, for example, at least one of an electrical characteristic and an optical characteristic. Further, each characteristic of the optical member 215 and the optical path unit 216 is, for example, an optical characteristic.

The interface unit 213 is able to include the calibration parameter signal S212 according to the parameter of the characteristic of the light receiving unit 211 (that is, the parameter according to the characteristic of the light receiving unit 211) in the output signal S213, and output the output signal S213 to the signal computation processing unit 23. Further, the interface unit 213 is able to include the calibration parameter signal S212 according to at least one (that is, at least one of the parameters according to the characteristics) stored in the storage unit 212 in the output signal S213, and output the output signal S213 to the signal computation processing unit 23. Specifically, the interface unit 213 is able to include the calibration parameter signal S212 according to the parameter according to the characteristic of the light receiving unit 211 and at least one of the parameters according to the characteristics of the component other than the light receiving unit 211 (each of the light emitting unit 214, the optical member 215, and the optical path unit 216) among the plurality of components provided in the signal output apparatus 21 in the output signal S213, and output the output signal S213 to the signal computation processing unit 23. Alternatively, the interface unit 213 is able to include the calibration parameter signal S212 according to at least one of the parameters according to the characteristics of the component other than the light receiving unit 211 (each of the light emitting unit 214, the optical member 215, and the optical path unit 216) among the plurality of components provided in the signal output apparatus 21 in the output signal S213, and output the output signal S213 to the signal computation processing unit 23 externally provided.

Here, the parameter according to the characteristic of the light receiving unit 211 may be a parameter for correcting a characteristic variation of the light receiving unit 211. The parameter according to the characteristic of the light emitting unit 214 may be a parameter for correcting a characteristic variation of the light emitting unit 214. The parameter according to the characteristic of the optical member 215 may be a parameter for correcting a characteristic variation of the optical member 215. The parameter according to the characteristic of the optical path unit 216 may be a parameter for correcting a characteristic variation of the optical path unit 216.

Further, the signal output apparatus 21 includes an integrated circuit 210 in which the storage unit 212 and the interface unit 213 are integrated, from the viewpoint of miniaturization. Meanwhile, the signal output apparatus 21 also may have a configuration in which the storage unit 212 and the interface unit 213 are not integrated.

As illustrated in FIG. 2, the concentration measurement system 2 according to the present embodiment includes the signal output apparatus 21 having the above configuration, and the signal computation processing unit 23 that is provided outside the signal output apparatus 21 and configured to compute the concentration of the measurement target substance on the basis of a signal based on the detection signal S211$d$ and the calibration parameter signal S212 included in the output signal S213 input from the interface unit 213, and a drive signal S214$dv$ for driving the light emitting unit 214.

The drive signal S214$dv$ for driving the light emitting unit 214 is input from the signal computation processing unit 23 to the interface unit 213. The interface unit 213 outputs the drive signal S214$dv$ input from the signal computation processing unit 23 to the light emitting unit 214. Therefore, the signal computation processing unit 23 outputs the drive signal S214$dv$ to the light emitting unit 214 via the interface unit 213. The drive signal S214$dv$ includes information for driving the light emitting unit 214. The drive signal S214$dv$ may be configured to include, for example, information such as a ratio of an operating time and a non-operating time (duty ratio) for pulse-driving the light emitting unit 214, and the current amount of a driving current flowing through the light emitting unit 214. The light emitting unit 214 operates based on the information included in the drive signal S214$dv$ input from the interface unit 213 to emit infrared rays.

The information included in the drive signal S214$dv$ output from the signal computation processing unit 23 may be stored in the storage unit 212 via the interface unit 213. In this case, the interface unit 213 generates the drive signal S214$dv$ based on the information input from the storage unit 212, and outputs the generated drive signal S214$dv$ to the light emitting unit 214. As a result, the concentration measurement system 2 is able to change a drive condition of the light emitting unit 214 in the signal output apparatus 21 without transmitting and receiving the drive signal S214$dv$ between the signal output apparatus 21 and the signal computation processing unit 23. Therefore, a load of the change process of the drive condition is able to be reduced.

The concentration measurement system 2 is able to output a concentration signal S23 corrected according to the characteristic peculiar to each of the plurality of components (the light receiving unit 211, the light emitting unit 214, the optical member 215, and the optical path unit 216 in the present embodiment) provided in the signal output apparatus 21. The signal computation processing unit 23 is able to generate and output the concentration signal S23 which is a signal resulting from concentration computation executed by using at least one of the parameters according to the respective characteristics of the light receiving unit 211, the light emitting unit 214, the optical member 215, and the optical path unit 216.

Here, the characteristic variation of the light receiving unit 111 is, for example, a variation in a photoelectric conversion characteristic due to a variation in electrical characteristics of a photodetector constituting a photoelectric conversion unit of the light receiving unit 111, a variation in a voltage or a current of the output signal due to a variation in electrical characteristics of a photodetector constituting an output unit of the light receiving unit 111, or the like. The characteristic variation of the light emitting unit 214 is, for example, a variation in a lightning conversion characteristic due to a variation in conversion efficiency of lightning conversion of the light emitting unit 214, or the like. The characteristic variation of the optical member 215 is, for example, a variation in a transmission characteristic due to a variation in a refractive index of members constituting the optical member 215, a variation in a refraction angle of the output infrared rays based on a variation in a transmitted central wavelength or a variation in a transmittance, or the like. A variation in the characteristic of the optical path unit 216 is, for example, a variation in an arrival loss of light, a variation in a reflectance of a material forming a reflecting unit that reflects infrared rays, a variation in a shape of the reflecting unit, or the like.

The signal computation processing unit 23 is configured to use information included in the drive signal S214$dv$ for the concentration computation of the measurement target substance, in addition to the respective characteristic variations of the light receiving unit 211, the light emitting unit 214, the optical member 215, and the optical path unit 216 constituting the signal output apparatus 21. As a result, the signal computation processing unit 23 is able to realize concentration computation with higher accuracy.

The calibration parameter signal S212 is not particularly limited as long as the concentration computation of the measurement target substance is able to be corrected as a result, according to the characteristic of at least one of the light receiving unit 211, the light emitting unit 214, the optical member 215, and the optical path unit 216. That is, the calibration parameter signal S212 is not particularly limited as long as the concentration computation of the measurement target substance is able to be corrected as a result, according to at least one of the characteristic variations of the light receiving unit 211, the light emitting unit 214, the optical member 215, and the optical path unit 216. In the same manner as the first embodiment, the calibration parameter signal S212 may be used as a coefficient of a predetermined equation in a case where the signal computation processing unit 23 applies the input detection signal S211 to, for example, the predetermined equation to compute the concentration.

In the signal output apparatus 21 according to the present embodiment, in the same manner as the signal output apparatus 11 in the first embodiment, the interface unit 213 includes the calibration parameter signal S212 in the output signal S213, and outputs the output signal S213 to the signal computation processing unit 23 externally provided, without executing the concentration computation of the measurement target substance. The interface unit 213 does not execute not only the concentration computation using the calibration parameter included in the calibration parameter signal S212 but also the concentration computation not using the calibration parameter. Here, the concentration computation includes correction of the output signal according to the concentration, in addition to the actual concentration computation. That is, the signal output apparatus 21 does not include a computation unit that computes based on the input signal. Therefore, the signal output apparatus 21 and the concentration measurement system 2 are able to reduce a thermal influence or an electromagnetic influence exerted on at least one of the light emitting unit 214 and the light receiving unit 211 by heat and electromagnetic waves generated by the computation operation of the computation unit. As a result, the concentration measurement system 2 is able to measure the concentration of the measurement target substance with high accuracy.

For example, the storage unit 212 stores a plurality of parameters according to the characteristics of at least one of the light receiving unit 211, the light emitting unit 214, the optical member 215, and the optical path unit 216 as the parameters according to the characteristics of at least one of the plurality of components included in the signal output apparatus 21 as calibration parameters. The storage unit 212 stores, for example, a parameter associated with a magnitude of the characteristic variation of at least one of the light receiving unit 211, the light emitting unit 214, the optical member 215, and the optical path unit 216 as the calibration parameter. In the same manner as the concentration measurement system 1 according to the first embodiment, in a shipping inspection of the concentration measurement system 2, concentration measurement of a standard measurement target substance having a known concentration is repeatedly executed while changing the parameters. The concentration measurement system 2 sets a parameter at which a concentration closest to the known concentration is obtained, as a calibration parameter used in actual operation. As a result, the concentration measurement system 2 is able to measure the concentration of the measurement target substance according to the characteristic of at least one of the light receiving unit 211, the light emitting unit 214, the optical member 215, and the optical path unit 216 (for example, the characteristic variation of at least one of the light receiving unit 211, the light emitting unit 214, the optical member 215, and the optical path unit 216). Such a setting of the calibration parameters according to the characteristic of at least one of the light receiving unit 211, the light emitting unit 214, the optical member 215, and the optical path unit 216 is not limited to the shipping inspection of the concentration measurement system 2, and may be executed before the operation of the concentration measurement system 2.

As described above, in addition to the configuration of the signal output apparatus 11 and the concentration measurement system 1 according to the first embodiment, the signal output apparatus 21 and the concentration measurement system 2 according to the present embodiment include the light emitting unit 214 that is provided at the support unit and emits infrared rays, and at least one of the optical member 215 provided in the support unit and disposed in the optical path through which the infrared rays emitted by the light emitting unit 214 reach the light receiving unit 211 or the optical path unit 216 that is provided in the support unit and guides the infrared rays emitted by the light emitting unit 214 to the light receiving unit 211 (all in the present embodiment). Further, the storage unit 212 provided in the signal output apparatus 21 is configured to store at least one of the parameter according to the characteristic of the light receiving unit 211, the parameter according to the characteristic of the light emitting unit 214, the parameter according to the characteristic of the optical member 215, or the parameter according to the characteristic of the optical path unit 216 as the parameter according to the characteristic of at least one of the plurality of components included in the signal output apparatus 21, as the calibration parameter. Further, the interface unit 213 is able to include the calibration parameter signal S212 according to the at least one stored in the storage unit 212 in the output signal S213, and output the output signal S213 to the signal computation processing unit 23.

As a result, since the concentration measurement system 2 is able to compute the concentration of the measurement target substance by using at least one of the parameters according to the characteristics of the light receiving unit 211, the light emitting unit 214, the optical member 215, and the optical path unit 216, the concentration of the measurement target substance is able to be computed with higher accuracy, as compared with the concentration measurement system 1 according to the first embodiment.

Further, the concentration measurement system 2 includes the signal computation processing unit 23 that is provided outside the signal output apparatus 21 and configured to compute the concentration of the measurement target substance on the basis of the signal based on the detection signal S211d and the calibration parameter signal S212 included in the output signal S213 input from the interface unit 213, and the drive signal S214dv for driving the light emitting unit 214.

As a result, the concentration measurement system 2 is able to compute the concentration of the measurement target substance with higher accuracy, as compared with the case where the drive signal S214dv is not used.

Modification Example

A signal output apparatus and a concentration measurement system according to a modification example of the present embodiment will be described with reference to FIG. 2 again. The concentration measurement system 2 according to the present modification example has a feature that a concentration of a measurement target substance is computed by using a parameter according to a complex characteristic of at least two of the parameters according to the characteristics of the light receiving unit 211, the light emitting unit 214, the optical member 215, and the optical path unit 216, as a parameter according to a complex characteristic of at least two of the characteristics of the plurality of components included in the signal output apparatus 21.

The storage unit 212 provided in the signal output apparatus 21 according to the present modification example stores the complex characteristic of at least two of the characteristics of the plurality of components (the light receiving unit 211, the light emitting unit 214, the optical member 215, and the optical path unit 216 in the present modification example) provided in the signal output apparatus 21, as a calibration parameter. The interface unit 213 is configured to include the calibration parameter signal S212 according to the parameter of the complex characteristic in the output signal S213, and output the output signal S213 to the signal computation processing unit 23 externally provided. The parameter according to the complex characteristic is a parameter for correcting a complex characteristic variation of at least two of the characteristic of the light receiving unit 211, the characteristic of the light emitting unit 214, the characteristic of the optical member 215, and the characteristic of the optical path unit 216.

In the signal output apparatus 21 according to the present modification example, the storage unit 212 stores the parameter according to the complex characteristic of at least two of the characteristic of the light receiving unit 211, the characteristic of the light emitting unit 214, the characteristic of the optical member 215, and the characteristic of the optical path unit 216, as the parameter according to the complex characteristic of at least two of the plurality of components included in the signal output apparatus 21, as the calibration parameters. As a result, the storage unit 212 is able to output the calibration parameter signal S212 according to the complex characteristic to the interface unit 213. Meanwhile, although the storage unit 212 may store the parameters according to at least two characteristics of the light receiving unit 211, the light emitting unit 214, the optical member 215, and the optical path unit 216, the parameters according to the complex characteristic may not be stored. In this case, the storage unit 212 outputs the calibration parameter signal S212 according to at least two stored parameters to the interface unit 213. The interface unit 213 may generate a parameter according to the complex characteristic obtained by combining the parameters included in the calibration parameter signal S212, and output the output signal S213 having the generated parameter according to the complex characteristic to the signal computation processing unit 23. Further, instead of the interface unit 213, the signal computation processing unit 23 may be configured to generate the parameter according to the complex characteristic obtained by combining the parameters included in the calibration parameter signal S212 included in the output signal S213.

The signal computation processing unit 23 provided in the concentration measurement system 2 according to the present modification example is able to compute the concentration of the measurement target substance by using the parameter according to the complex characteristic included in the output signal S213 input from the interface unit 213. As described above, in the concentration measurement system 2 according to the present modification example, even when the signal output apparatus 21 has the complex characteristic variation in which at least two characteristic variations of the light receiving unit 211, the light emitting unit 214, the optical member 215, and the optical path unit 216 are combined, it is possible to calibrate the concentration computation of the measurement target substance. As a result, the concentration measurement system 2 according to the present modification example is able to improve the measurement accuracy of the concentration of the measurement target substance.

Third Embodiment

Figure 3:
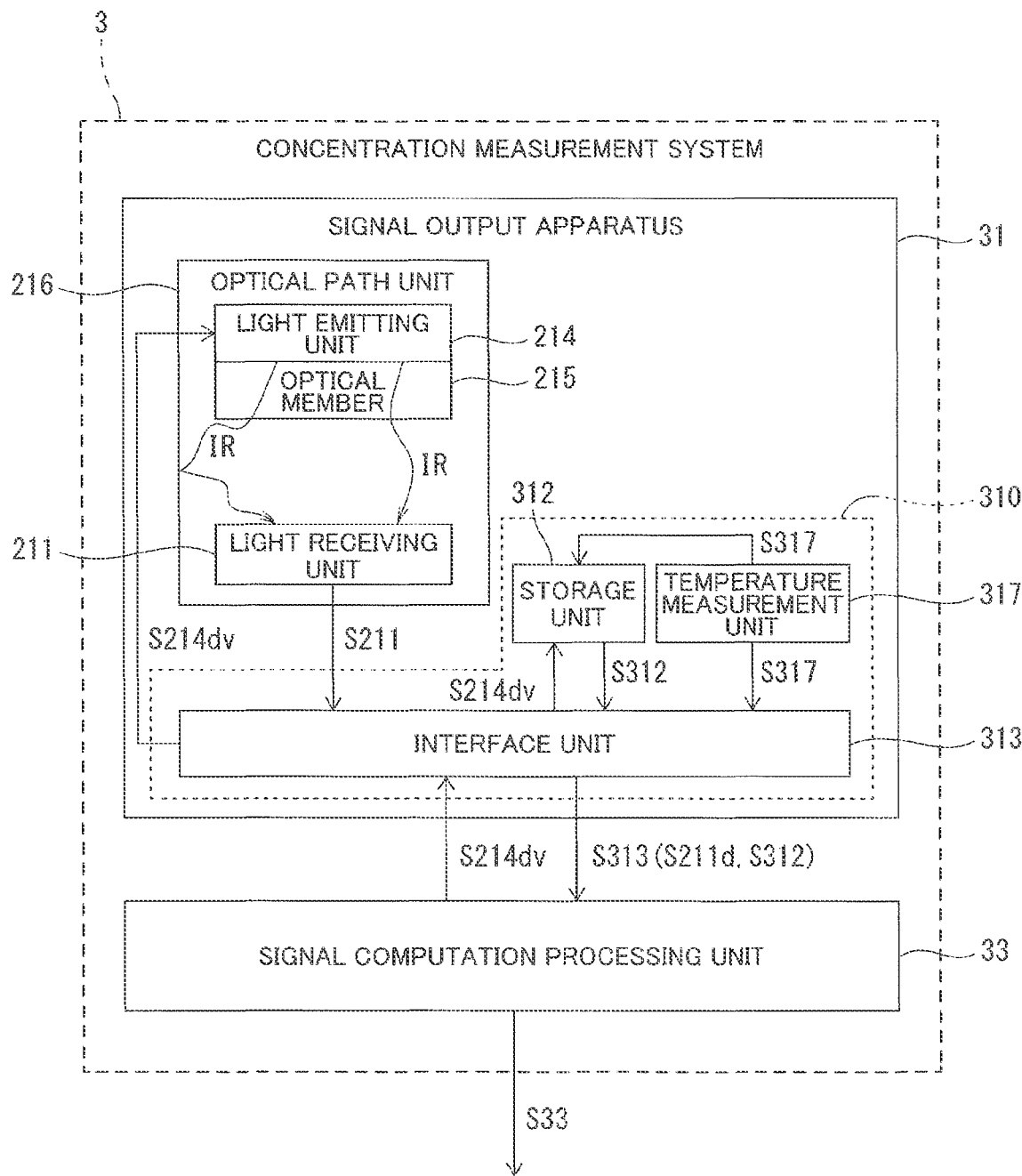
FIG. 3 is a block diagram illustrating an example of a schematic configuration of a signal output apparatus and a concentration measurement system according to a third embodiment of the present invention.

A signal output apparatus and a concentration measurement system according to the third embodiment of the present invention will be described with reference to FIG. 3 and FIG. 4. FIG. 3 is a block diagram illustrating an example of a schematic configuration of a signal output apparatus 31 and a concentration measurement system 3 according to the present embodiment. FIG. 4 is a schematic cross-sectional view illustrating an example of a schematic configuration of the concentration measurement system 3 according to the present embodiment. Hereinafter, as the signal output apparatus according to the present embodiment, the signal output apparatus 31 for the concentration measurement system will be described as an example. Further, in description of the signal output apparatus 31 and the concentration measurement system 3 according to the present embodiment, the same reference numerals are given to the components having the same actions and functions as the signal output apparatus 21 and the concentration measurement system 2 according to the second embodiment, and the description thereof will be omitted.

As illustrated in FIG. 3, the signal output apparatus 31 according to the present embodiment includes the light receiving unit 211 that receives infrared rays emitted to a measurement target substance, and outputs the detection signal S211 according to the received infrared rays. In addition, the signal output apparatus 31 includes a storage unit 312 that stores a parameter according to a characteristic of at least one of the plurality of components including the light receiving unit 211, the parameter being used for computing a concentration of the measurement target substance, as a calibration parameter. Further, the signal output apparatus 31 includes an interface unit 313 capable of outputting an output signal S313 including a calibration parameter signal S312 according to the calibration parameter input from the storage unit 312 and a signal based on the detection signal S211 input from the light receiving unit 211 to a signal computation processing unit 33 externally provided, without executing concentration computation. The interface unit 313 is electrically connected to the light receiving unit 211 and the storage unit 312. The signal output apparatus 31 includes a support unit 318 that supports the light receiving unit 211, the storage unit 312, and the interface unit 313 (see FIG. 4).

The concept of "output signal S313 includes calibration parameter signal S312 and signal based on detection signal S211" has the same concept of "output signal S113 includes calibration parameter signal S112 and signal based on detection signal S111" in the first embodiment. Further, in the same manner as the interface unit 113 in the first embodiment, the interface unit 313 may be configured to have a function of amplifying the input detection signal S211 and analog-to-digital converting the amplified detection signal S211 to generate a digital detection signal S211$d$. In this case, the output signal S313 includes the digital detection signal S211$d$. The interface unit 313 may be configured to amplify the detection signal S211 or perform analog-to-digital conversion, and is configured not to execute a computation process of the detection signal S211.

Here, the output signal S313 includes the digital detection signal S211$d$. The analog detection signal S211 output from the light receiving unit 211 and the digital detection signal S211$d$ are signals having identical information except for signal formats different from each other. Therefore, in the present embodiment, the signal based on the detection signal S211 means a signal actually included, between the analog detection signal S211 and the digital detection signal S211$d$. That is, in a case where the output signal S313 includes the digital detection signal S211$d$ as in the present embodiment, the signal based on the detection signal S211 becomes the detection signal S211$d$. On the other hand, in a case where the output signal S313 includes the analog detection signal S211, the signal based on the detection signal S211 becomes the detection signal S211.

The signal output apparatus 31 further includes a temperature measurement unit 317 that measures a temperature. The temperature measurement unit 317 measures, for example, a temperature of the light emitting unit 214. The temperature measurement unit 317 may be configured with, for example, a thermistor, a thermocouple, a diode, or another element capable of measuring the temperature.

The temperature measurement unit 317 is configured to output a temperature signal S317 according to the measured temperature to the storage unit 312. The storage unit 312 is configured to store parameters related to the temperature as calibration parameters, and to output a calibration parameter signal S312 according to the parameter corresponding to the temperature input from the temperature measurement unit 317 to the interface unit 313. More specifically, when the temperature signal S317 according to the temperature is input from the temperature measurement unit 317 to the storage unit 312, the storage unit 312 selects a parameter related to the temperature associated with the input temperature signal S317, and outputs the calibration parameter signal S312 according to the selected parameter to the interface unit 313.

As illustrated in FIG. 3, in addition to the light receiving unit 211, the signal output apparatus 31 includes at least one of the light emitting unit 214, the optical member 215 or the optical path unit 216, as the plurality of components. That is, the signal output apparatus 31 according to the present embodiment includes the light receiving unit 211, the light emitting unit 214, the optical member 215, and the optical path unit 216, as the plurality of components. Here, the light emitting unit 214, the optical member 215, and the optical path unit 216 are also supported by the support unit 318 (see FIG. 4). The storage unit 312 stores parameters according to the characteristic of the light receiving unit 211 as parameters according to a characteristic of at least one of the plurality of components included in the signal output apparatus 31, as the calibration parameters. Further, the storage unit 312 stores at least one of parameters according to characteristics of components other than the light receiving unit 211 among the plurality of components included in the signal output apparatus 31, as the calibration parameters. In the present embodiment, the light emitting unit 214, the optical member 215, and the optical path unit 216 correspond to the plurality of components other than the light receiving unit 211. As a result, the storage unit 312 is able to output the calibration parameter signal S312 according to at least one of the parameter according to the characteristic of the light receiving unit 211, the parameter according to the characteristic of the light emitting unit 214, the parameter according to the characteristic of the optical member 215, and the parameter according to the characteristic of the optical path unit 216 to the interface unit 313. Each characteristic of the light receiving unit 211, the light emitting unit 214, the optical member 215, and the optical path unit 216 is the same as each characteristic of the light receiving unit 211, the light emitting unit 214, the optical member 215, and the optical path unit 216 in the second embodiment.

The interface unit 313 is able to include the calibration parameter signal S212 according to the parameter of the characteristic of the light receiving unit 211 (that is, the parameter according to the characteristic of the light receiving unit 211) in the output signal S213, and output the output signal S213 to the signal computation processing unit 23. Further, the interface unit 313 is able to include the calibration parameter signal S212 according to at least one stored in the storage unit 212 (that is, at least one of the respective parameters according to the characteristics of the light emitting unit 214, the optical member 215, and the optical path unit 216) in the output signal S213, and output the output signal S213 to the signal computation processing unit 23. In addition, the interface unit 313 is able to include the calibration parameter signal S312 according to the parameter according to the temperature in the output signal S313, and output the output signal S313 to the signal computation processing unit 23. Further, the interface unit 313 is able to include the calibration parameter signal S312 according to at least one of the characteristic of the light receiving unit 211, the characteristic of the light emitting unit 214, the characteristic of the optical member 215, the characteristic of the optical path unit 216, and the temperature in the output signal S313, and output the output signal S313 to the signal computation processing unit 23 externally provided. The parameters according to the respective characteristics of the light receiving unit 211, the light emitting unit 214, the optical member 215, and the optical path unit 216 may be calibration parameters for respective characteristic variations of the light receiving unit 211, the light emitting unit 214, the optical member 215, and the optical path unit 216, in the same manner as the second embodiment.

From the viewpoint of miniaturization, the signal output apparatus 31 includes an integrated circuit 310 in which the storage unit 312, the interface unit 313, and the temperature measurement unit 317 are integrated. Meanwhile, the signal output apparatus 31 also may have a configuration in which the storage unit 312, the interface unit 313, and the temperature measurement unit 317 are not integrated.

As illustrated in FIG. 3, the concentration measurement system 3 according to the present embodiment includes the signal output apparatus 31 having the above configuration, and the signal computation processing unit 33 that is provided outside the signal output apparatus 31 and configured to compute the concentration of the measurement target substance on the basis of a signal based on the detection signal S211d and the calibration parameter signal S312 included in the output signal S313 input from the interface unit 313, and the drive signal S214dv for driving the light emitting unit 214. Further, in a case where the calibration parameter signal S312 included in the output signal S313 has a parameter according to the temperature, the signal computation processing unit 33 is configured to compute the concentration of the measurement target substance by using other parameters and the parameter according to the temperature.

The concentration measurement system 3 is able to output a concentration signal S33 corrected according to the characteristic peculiar to each of the plurality of components (the light receiving unit 211, the light emitting unit 214, the optical member 215, and the optical path unit 216 in the present embodiment) provided in the signal output apparatus 21, and the temperature measured by the temperature measurement unit 317. The signal computation processing unit 33 is able to generate and output the concentration signal S33 which is a signal resulting from concentration computation executed by using at least one of the parameters according to the respective characteristics of the light receiving unit 211, the light emitting unit 214, the optical member 215, and the optical path unit 216, and the parameter according to the temperature.

The signal computation processing unit 33 is configured to use the temperature measured by the temperature measurement unit 317 for the concentration computation of the measurement target substance, in addition to the information included in the drive signal S214dv, and the respective characteristic variations of the light receiving unit 211, the light emitting unit 214, the optical member 215, and the optical path unit 216 constituting the signal output apparatus 31. As a result, the signal computation processing unit 23 is able to realize concentration computation with higher accuracy.

Further, the temperature measurement unit 317 may be configured to output the temperature signal S317 to the signal computation processing unit 33 via the interface unit 313. In this case, the signal computation processing unit 33 stores parameters related to the temperature in association with the temperature. The signal computation processing unit 33 is able to select a parameter related to the temperature corresponding to the temperature signal S317 input from the temperature measurement unit 317, and use the selected parameter to correct the concentration computation of the measurement target substance.

The calibration parameter signal S312 is not particularly limited as long as the concentration computation of the measurement target substance is able to be corrected as a result, according to at least one of the temperature measured by the temperature measurement unit 317, the information included in the drive signal S214dv, and at least one characteristic of the light receiving unit 211, the light emitting unit 214, the optical member 215, and the optical path unit 216. That is, the calibration parameter signal S312 is not particularly limited as long as the concentration computation of the measurement target substance is able to be corrected as a result, according to at least one of the temperature of the signal output apparatus 31 (mainly the temperature of the light emitting unit 214), the drive information of the light emitting unit 214, and at least one characteristic variation of the light receiving unit 211, the light emitting unit 214, the optical member 215, and the optical path unit 216. In the same manner as the second embodiment, the calibration parameter signal S312 may be used as a coefficient of a predetermined equation in a case where the signal computation processing unit 33 applies the input detection signal S211 to, for example, the predetermined equation to compute the concentration. Here, in a case where the predetermined equation is able to be expressed by the cubic function of "$y = a \times x^3 + b \times x^2 + c \times x + d$", the coefficients a, b, c, and d may be parameters of the calibration parameter signal (that is, the calibration parameters stored in the storage unit 212). In the cubic function, y may be a concentration result of the measurement target substance, and x may be a signal according to the detection signal S211 output from the light receiving unit 111 or the temperature signal S317 output from the temperature measurement unit 317.

In the signal output apparatus 31 according to the present embodiment, in the same manner as the signal output apparatus 21 in the second embodiment, the interface unit 313 includes the calibration parameter signal S312 in the output signal S313, and outputs the output signal S313 to the signal computation processing unit 33 externally provided, without executing the concentration computation of the measurement target substance. The interface unit 313 does not execute not only the concentration computation using the calibration parameter included in the calibration parameter signal S312 but also the concentration computation not using the calibration parameter. Here, the concentration computation includes correction of the output signal according to the concentration, in addition to the actual concentration computation. That is, the signal output apparatus 31 does not include a computation unit that computes based on the input signal. Therefore, the signal output apparatus 31 and the concentration measurement system 3 are able to reduce a thermal influence or an electromagnetic influence exerted on at least one of the light emitting unit 214 and the light receiving unit 211 by heat and electromagnetic waves generated by the computation operation of the computation unit. As a result, the concentration measurement system 3 is able to measure the concentration of the measurement target substance with high accuracy.

As described above, in the same manner as the concentration measurement system 2 according to the second embodiment, the concentration measurement system 3 is able to compute the concentration of the measurement target substance by using at least one parameter of the respective characteristics (for example, characteristic variations) of the light receiving unit 211, the light emitting unit 214, the optical member 215, and the optical path unit 216, and the detection signal S211 configured with the drive information of the light emitting unit 214 included in the drive signal S214dv. Further, the concentration measurement system 3 is able to use the calibration parameter signal S312 capable of correcting a characteristic fluctuation caused by the temperature. As a result, the concentration measurement system 3 is able to realize concentration measurement with higher accuracy.

Next, an example of a structure of the signal output apparatus 31 and the concentration measurement system 3 according to the present embodiment will be described with reference to FIG. 4. In FIG. 4, a structure of the signal computation processing unit 33 provided in the concentration measurement system 3 is not illustrated, and the signal computation processing unit 33 is illustrated in a block format.

As illustrated in FIG. 4, the signal output apparatus 31 includes the support unit 318 that supports the light receiving unit 211, the storage unit 312, the light emitting unit 214, the temperature measurement unit 317, the interface unit 313, and, the wiring unit 319. The support unit 318 is made of, for example, resin, and the light receiving unit 211, the storage unit 312, the light emitting unit 214, the temperature measurement unit 317, the interface unit 313, and the wiring unit 319 are sealed by the support unit 318. As described above, the signal output apparatus 31 has a structure in which the light receiving unit 211 and the like are packaged by the support unit 318. The light receiving unit 211, the storage unit 312, the light emitting unit 214, the temperature measurement unit 317, the interface unit 313, and the wiring unit 319 are electrically connected to each other inside the support unit 318 via a conductive wire (not illustrated). The integrated circuit 310 has the storage unit 312, the temperature measurement unit 317, and the interface unit 313 in the same package. The wiring unit 319 has a plurality of terminals electrically independent from each other (not illustrated). The terminal is connected to the signal computation processing unit 33 via a metal bump, wiring of a mounting substrate, or the like (neither is illustrated). As a result, the concentration measurement system 3 enables transmission of the output signal S313 from the interface unit 313 to the signal computation processing unit 33, and transmission of the drive signal S214dv from the signal computation processing unit 33 to the interface unit 313.

The optical member 215 is disposed on the support unit 318 to cover parts of the light emitting unit 214 and the wiring unit 319. Further, the optical path unit 216 is disposed to cover the entire support unit 318 and the optical member 215, and the optical path unit 216 is supported by the support unit 318. The optical path unit 216 has a spherical recess portion from a central portion to a peripheral portion. The optical path unit 216 is disposed so that the recess portion faces the support unit 318. As a result, the signal output apparatus 31 has a space portion 35 formed between the optical path unit 216 and the support unit 318. A vent hole 216b penetrating the optical path unit 216 is formed in the optical path unit 216. The vent hole 216b is formed directly above the support unit 318 in a state in which a part of a surface of the support unit 318 is exposed in a space of the vent hole 216b, and the vent hole 216b may be formed at another location of the optical path unit 216. For example, a gas of the measurement target substance is introduced from the vent hole 216b into the space portion 35, and the gas is discharged to the outside of the space portion 35 through the vent hole 216b.

A surface 216a of the optical path unit 216 on the space portion 35 side has a curved surface shape. The infrared rays emitted by the light emitting unit 214 are incident on the optical member 215 with a predetermined spread. The optical path unit 216 is disposed to be exposed to the space portion 35. Therefore, the infrared rays passing through the optical member 215 are emitted from the optical member 215 to the space portion 35 with a predetermined spread. Since the surface 216a of the optical path unit 216 has the curved surface shape, the infrared rays emitted from the optical member 215 with the predetermined spread are reflected by the surface 216a once or a plurality of times, and guided to the light receiving unit 211 disposed to be exposed to the space portion 35.

The concentration measurement system 3 according to the present embodiment has a form in which the signal output apparatus 31 and the signal computation processing unit 33 are separated. Therefore, as compared with a form in which the signal computation processing unit is provided inside the signal output apparatus and packaged with a sealing member, since the concentration measurement system 3 reduces at least one of the thermal and electromagnetic influences emitted from the signal computation processing unit 33 and stores the calibration parameters in the storage unit 312, it is possible for the concentration measurement system 3 as a whole to perform concentration measurement with high accuracy. Further, the concentration measurement system 3 is able to be easily assembled by simply attaching the signal output apparatus 31 to a mounting substrate or the like. The signal output apparatus 21 and the concentration measurement system 2 according to the second embodiment may have a structure in the same manner as the structure illustrated in FIG. 4, except that the signal output apparatus 21 and the concentration measurement system 2 do not have the temperature measurement unit 317.

As described above, the signal output apparatus 31 and the concentration measurement system 3 according to the present embodiment include the temperature measurement unit 317 that measures a temperature, in addition to the configuration of the signal output apparatus 21 and the concentration measurement system 2 according to the second embodiment. Further, information on the temperature measured by the temperature measurement unit 317 is input to the storage unit 312 provided in the signal output apparatus 31. The storage unit 312 is able to output the calibration parameter signal S312 according to a parameter corresponding to the temperature associated with the information on the input temperature to the interface unit 313. The interface unit 313 is able to output the output signal S313 including a calibration parameter signal according to the parameter corresponding to the temperature to the signal computation processing unit 23.

As a result, the signal output apparatus 31 and the concentration measurement system 3 have the same effects as the signal output apparatus 21 and the concentration measurement system 2 according to the second embodiment. Further, since the concentration measurement system 3 is able to correct the characteristic fluctuation caused by the temperature, it is possible to compute the concentration of the measurement target substance with higher accuracy.

Modification Example

A signal output apparatus and a concentration measurement system according to a modification example of the present embodiment will be described with reference to FIG. 3 again. In the same manner as the concentration measurement system 2 according to the modification example of the second embodiment, the concentration measurement system 3 according to the present modification example has a feature that a concentration of a measurement target substance is computed by using the parameter according to the complex characteristic of at least two of the parameters according to the characteristics of the light receiving unit 211, the light emitting unit 214, the optical member 215, and the optical path unit 216.

The storage unit 312 provided in the signal output apparatus 31 according to the present modification example stores the complex characteristic of at least two of the characteristics of the components (the light emitting unit 214, the optical member 215, and the optical path unit 216 in the present modification example) provided in the signal output apparatus 31 and the characteristic of the light receiving unit 211, as calibration parameters. The interface unit 313 is configured to include the calibration parameter signal S312 according to the parameter of the complex characteristic in the output signal S313, and output the output signal S313 to the signal computation processing unit 33 externally provided. The parameter according to the complex characteristic in the present modification example is the same as the parameter according to the complex characteristic in the modification example of the second embodiment.

The storage unit 312 is able to output the calibration parameter signal S312 according to the complex characteristic to the interface unit 313. Meanwhile, although the storage unit 312 may store the parameters according to at least two characteristics of the light receiving unit 211, the light emitting unit 214, the optical member 215, and the optical path unit 216, the parameters according to the complex characteristic may not be stored. In this case, the storage unit 312 outputs the calibration parameter signal S312 according to at least two stored parameters to the interface unit 313. The interface unit 313 may generate a parameter according to the complex characteristic obtained by combining the parameters included in the calibration parameter signal S312, and output the output signal S313 having the generated parameter according to the complex characteristic to the signal computation processing unit 33. Further, instead of the interface unit 313, the signal computation processing unit 33 may be configured to generate the parameter according to the complex characteristic obtained by combining the parameters included in the calibration parameter signal S312 included in the output signal S313.

The signal computation processing unit 33 provided in the concentration measurement system 3 according to the present modification example is able to compute the concentration of the measurement target substance by using the parameter according to the complex characteristic included in the output signal S313 input from the interface unit 313. As described above, in the concentration measurement system 3 according to the present modification example, even when the signal output apparatus 31 has the complex characteristic variation in which at least two characteristic variations of the light receiving unit 211, the light emitting unit 214, the optical member 215, and the optical path unit 216 are combined, it is possible to correct the concentration computation of the measurement target substance. As a result, the concentration measurement system 3 according to the present modification example is able to improve the measurement accuracy of the concentration of the measurement target substance.

Next, another modification example of the signal output apparatus 31 and the concentration measurement system 3 according to the present embodiment will be described with reference to FIG. 5. In FIG. 5, a structure of a signal computation processing unit 33 provided in a concentration measurement system 4 according to the present modification example is not illustrated, and the signal computation processing unit 33 is illustrated in a block format. In description of a signal output apparatus 41 and the concentration measurement system 4 according to the present modification example, the same reference numerals are given to the components having the same actions and functions as the signal output apparatus 31 and the concentration measurement system 3 according to the third embodiment, and the description thereof will be omitted.

As illustrated in FIG. 5, the signal output apparatus 41 includes a light receiving unit 411, a storage unit 412, a light emitting unit 414, an interface unit 413, and a support unit 418 that supports the light receiving unit 411, the storage unit 412, the light emitting unit 414, and the interface unit 413. The support unit 418 may be made of, for example, resin, and may be metal, ceramic, or the like.

In the signal output apparatus 41 according to the present modification example, the light receiving unit 411, the storage unit 412, the light emitting unit 414, and the interface unit 413 are independently provided on the support unit 418. Here, the light receiving unit 411, the storage unit 412, the light emitting unit 414, and the interface unit 413 are supported by the support unit 418 in a state of being respectively and independently sealed by a sealing member 420. The light emitting unit 414 is sealed by the sealing member 420 in a state in which a region (not illustrated) that emits infrared rays is exposed to the space portion 35. The light receiving unit 411 is sealed by the sealing member 420 in a state in which a light receiving region (not illustrated) that receives the infrared rays reflected by the surface 216a of the optical path unit 216 is exposed to the space portion 35. The storage unit 412 and the interface unit 413 are sealed by the sealing member 420 in a state of not being exposed to the space portion 35. The light receiving unit 411, the storage unit 412, the light emitting unit 414, and the interface unit 413 are electrically connected via a wiring (not illustrated) provided at the support unit 418.

Although the light receiving unit 411, the storage unit 412, the light emitting unit 414, and the interface unit 413 are respectively and independently sealed by the sealing member 420, two or more of the light receiving unit 411, the storage unit 412, the light emitting unit 414, and the interface unit 413 may be sealed by one sealing member 420, and for example, the light receiving unit 411 and the interface unit 413 may be sealed by one sealing member 420.

REFERENCE MARKS IN THE DRAWINGS 1, 2, 3, 4 concentration measurement system
11, 21, 31, 41 signal output apparatus
13, 23, 33 signal computation processing unit
35 space portion
110, 210, 310 integrated circuit
111, 211, 411 light receiving unit
112, 212, 312, 412 storage unit
113, 213, 313, 413 interface unit
214, 414 light emitting unit
215 optical member 216 optical path unit
216a surface
216b vent hole
317 temperature measurement unit
318, 418 support unit
319 wiring unit
420 sealing member
S13, S23, S33 concentration signal
S111, S111d, S211, S211d detection signal
S112, S212, S312 calibration parameter signal
S113, S213, S313 output signal
S214dv drive signal
S311 detection signal
S317 temperature signal

What is claimed is:

1. A signal output apparatus comprising:
a support unit;
a light receiving unit provided at the support unit, and configured to receive infrared rays emitted to a measurement target substance, and output a detection signal according to the received infrared rays;
a storage unit provided at the support unit, and configured to store a parameter according to a characteristic of at least one of a plurality of components including the light receiving unit, the parameter being used for concentration computation of the measurement target substance, as a calibration parameter; and
an interface unit provided at the support unit, and configured to output an output signal including a calibration parameter signal according to the calibration parameter input from the storage unit and a signal based on the detection signal input from the light receiving unit to a signal computation processing unit externally provided, without executing the concentration computation.

2. The signal output apparatus according to claim 1, wherein the storage unit stores a parameter according to a characteristic of the light receiving unit among the plurality of components as the calibration parameter.

3. The signal output apparatus according to claim 2, wherein the interface unit outputs the output signal including the calibration parameter signal according to the parameter of the characteristic of the light receiving unit to the signal computation processing unit.

4. The signal output apparatus according to claim 3, wherein the plurality of components include, in addition to the light receiving unit,
at least one of a light emitting unit provided at the support unit and configured to emit infrared rays, an optical member provided at the support unit and disposed in an optical path through which the infrared rays emitted by the light emitting unit reach the light receiving unit, or an optical path unit provided at the support unit, and configured to guide the infrared rays emitted by the light emitting unit to the light receiving unit,
the storage unit stores at least one of parameters according to characteristics of the provided plurality of components as the calibration parameter, and
the interface unit outputs the output signal including the calibration parameter signal according to the at least one parameter stored in the storage unit to the signal computation processing unit.

5. The signal output apparatus according to claim 3, wherein the plurality of components include, in addition to the light receiving unit,
at least one of a light emitting unit provided at the support unit and configured to emit infrared rays, an optical member provided at the support unit and disposed in an optical path through which the infrared rays emitted by the light emitting unit reach the light receiving unit, or an optical path unit provided at the support unit, and configured to guide the infrared rays emitted by the light emitting unit to the light receiving unit,
the storage unit stores a parameter according to a complex characteristic of at least two of characteristics of the provided plurality of components as the calibration parameter, and
the interface unit outputs the output signal including the calibration parameter signal according to the parameter of the complex characteristic to the signal computation processing unit.

6. The signal output apparatus according to claim 2, wherein the plurality of components include, in addition to the light receiving unit,
at least one of a light emitting unit provided at the support unit and configured to emit infrared rays, an optical member provided at the support unit and disposed in an optical path through which the infrared rays emitted by the light emitting unit reach the light receiving unit, or an optical path unit provided at the support unit, and configured to guide the infrared rays emitted by the light emitting unit to the light receiving unit,
the storage unit stores at least one of parameters according to characteristics of the provided plurality of components as the calibration parameter, and
the interface unit outputs the output signal including the calibration parameter signal according to the at least one parameter stored in the storage unit to the signal computation processing unit.

7. The signal output apparatus according to claim 6, wherein the parameter according to the characteristic of the light receiving unit is a parameter for correcting a characteristic variation of the light receiving unit,
a parameter according to a characteristic of the light emitting unit is a parameter for correcting a characteristic variation of the light emitting unit,
a parameter according to a characteristic of the optical member is a parameter for correcting a characteristic variation of the optical member, and
a parameter according to a characteristic of the optical path unit is a parameter for correcting a characteristic variation of the optical path unit.

8. A concentration measurement system comprising:
the signal output apparatus according to claim 4; and
the signal computation processing unit provided outside the signal output apparatus and configured to compute a concentration of the measurement target substance on the basis of the signal based on the detection signal and the calibration parameter signal included in the output signal input from the interface unit, and a drive signal for driving the light emitting unit.

9. The concentration measurement system according to claim 8, wherein the interface unit outputs the drive signal to the light emitting unit.

10. The concentration measurement system according to claim 8, wherein the signal output apparatus includes an integrated circuit in which the storage unit and the interface unit are integrated.

11. The concentration measurement system according to claim 8, wherein the signal output apparatus further includes a temperature measurement unit configured to measure a temperature.

12. The concentration measurement system according to claim 11, wherein the storage unit stores a parameter related to the temperature as the calibration parameter, and outputs the calibration parameter signal according to the parameter corresponding to the temperature input from the temperature measurement unit to the interface unit.

13. The concentration measurement system according to claim 11, wherein the signal output apparatus includes an integrated circuit in which the storage unit, the interface unit, and the temperature measurement unit are integrated.

14. The signal output apparatus according to claim 2,
wherein the plurality of components include, in addition to the light receiving unit,
at least one of a light emitting unit provided at the support unit and configured to emit infrared rays, an optical member provided at the support unit and disposed in an optical path through which the infrared rays emitted by the light emitting unit reach the light receiving unit, or an optical path unit provided at the support unit and configured to guide the infrared rays emitted by the light emitting unit to the light receiving unit,
the storage unit stores a parameter according to a complex characteristic of at least two of characteristics of the provided plurality of components as the calibration parameter, and
the interface unit outputs the output signal including the calibration parameter signal according to the parameter of the complex characteristic to the signal computation processing unit.

15. The signal output apparatus according to claim 14, wherein the parameter according to the complex characteristic is a parameter for correcting a complex characteristic variation of at least two of the characteristic of the light receiving unit, a characteristic of the light emitting unit, a characteristic of the optical member, and a characteristic of the optical path unit.

16. The signal output apparatus according to claim 1, comprising:
an integrated circuit in which the storage unit and the interface unit are integrated.

17. The signal output apparatus according to claim 1, further comprising:
a temperature measurement unit provided at the support unit, and configured to measure a temperature.

18. The signal output apparatus according to claim 17, wherein the storage unit stores a parameter related to a temperature as the calibration parameter, and outputs the calibration parameter signal according to the parameter corresponding to the temperature input from the temperature measurement unit to the interface unit.

19. The signal output apparatus according to claim 17, comprising:
an integrated circuit in which the storage unit, the interface unit, and the temperature measurement unit are integrated.

20. A concentration measurement system comprising:
the signal output apparatus according to claim 1; and
the signal computation processing unit provided outside the signal output apparatus and configured to compute a concentration of the measurement target substance on the basis of the signal based on the detection signal and the calibration parameter signal included in the output signal input from the interface unit.

* * * * *